US011188956B2

(12) United States Patent
Webb et al.

(10) Patent No.: US 11,188,956 B2
(45) Date of Patent: Nov. 30, 2021

(54) SYSTEM AND METHOD FOR PERFORMING OPERATIONS IN RESPONSE TO PREAUTHORIZATION AND GEOGRAPHIC LOCATION DATA

(71) Applicant: Walmart Apollo, LLC, Bentonville, AR (US)

(72) Inventors: Timothy W. Webb, Rogers, AR (US); Jason R. Todd, Lowell, AR (US); Rebecca Schmalbeck, Bella Vista, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 305 days.

(21) Appl. No.: 15/109,065

(22) PCT Filed: Jan. 8, 2015

(86) PCT No.: PCT/US2015/010674
§ 371 (c)(1),
(2) Date: Jun. 29, 2016

(87) PCT Pub. No.: WO2015/106009
PCT Pub. Date: Jul. 16, 2015

(65) Prior Publication Data
US 2016/0328536 A1 Nov. 10, 2016

Related U.S. Application Data

(60) Provisional application No. 61/924,815, filed on Jan. 8, 2014.

(51) Int. Cl.
*G06Q 30/04* (2012.01)
*G16H 10/60* (2018.01)
*G16H 20/10* (2018.01)

(52) U.S. Cl.
CPC ........... *G06Q 30/04* (2013.01); *G16H 10/60* (2018.01); *G16H 20/10* (2018.01)

(58) Field of Classification Search
None
See application file for complete search history.

(56) References Cited

U.S. PATENT DOCUMENTS

| | | |
|---|---|---|
| 8,626,530 B1 * | 1/2014 | Tran ............. G06Q 10/087 705/2 |
| 2006/0094447 A1 * | 5/2006 | Zellner ............. H04L 41/12 455/456.3 |

(Continued)

FOREIGN PATENT DOCUMENTS

WO WO-2007084955 A2 * 7/2007 ............ G16H 20/10

OTHER PUBLICATIONS

Joy M Grossman et al., Transmitting and processing electronic prescriptions: experiences of physician practices and pharmacies, 19 Journal of the American Medical Informatics Association 353-359 (2011) (Year: 2011).*

(Continued)

*Primary Examiner* — Devin C Hein
*Assistant Examiner* — Nicholas Akogyeram, II
(74) *Attorney, Agent, or Firm* — Fitch, Even, Tabin & Flannery LLP (57) ABSTRACT

A system for purchasing performing operations in response to preauthorization and receiving geographic coordinates. The system includes, but is not limited to, a remote server, communicatively coupled to a third party system and a user database. The remote server is configured to query the user database to retrieve a unique identifier associated with the user and with prescription information for the user. The remote server includes a link in the unique identifier and transmits a message including the unique identifier to a local (Continued)

device associated with the user. The remote server receives instructions from the local device and obtains preauthorization from the third party system in response to the instructions. Furthermore, the remote server receives and tracks geographic coordinates of the local device. In response to preauthorization and tracking the geographic coordinates, initiate operations in preparation for arrival of the user.

14 Claims, 4 Drawing Sheets

(56) References Cited

U.S. PATENT DOCUMENTS

| | | | | |
|---|---|---|---|---|
| 2007/0168228 A1* | 7/2007 | Lawless | ............... | G06Q 50/24 705/2 |
| 2010/0250271 A1* | 9/2010 | Pearce | ............... | G16H 40/67 705/2 |
| 2010/0305974 A1* | 12/2010 | Patch | ............... | G06Q 50/22 705/3 |
| 2011/0071847 A1* | 3/2011 | Keresman, III | ....... | G06Q 50/22 705/2 |
| 2011/0288881 A1* | 11/2011 | Machani | ............... | G06Q 50/22 705/2 |
| 2012/0041781 A1* | 2/2012 | Louie | ............... | G06F 19/3462 705/2 |
| 2013/0226651 A1* | 8/2013 | Napper | ............... | G06Q 30/06 705/7.26 |
| 2013/0325494 A1* | 12/2013 | Angel | ............... | G06Q 30/00 705/2 |
| 2013/0339045 A1* | 12/2013 | Lockhart | ........... | G06Q 30/0631 705/2 |
| 2013/0347129 A1* | 12/2013 | Samuelsson | ............ | H04L 9/321 726/28 |
| 2014/0006055 A1* | 1/2014 | Seraly | ............... | G16H 10/60 705/2 |
| 2014/0046908 A1* | 2/2014 | Patiejunas | ............. | G06Q 20/12 705/14.56 |
| 2014/0214437 A1* | 7/2014 | Ammerman | ........... | G16H 10/60 705/2 |
| 2014/0324588 A1* | 10/2014 | Killoran, Jr. | ......... | G06Q 10/107 705/14.56 |

OTHER PUBLICATIONS

International Search Report and Written Opinion from corresponding PCT/US2015/010674 dated Apr. 10, 2015.
International Preliminary Report on Patentability issued in related international patent application No. PCT/US2015/010674 dated Jul. 21, 2016.

\* cited by examiner

SYSTEM AND METHOD FOR PERFORMING OPERATIONS IN RESPONSE TO PREAUTHORIZATION AND GEOGRAPHIC LOCATION DATA

CROSS-REFERENCE TO RELATED PATENT APPLICATIONS

This application is a 35 U.S.C. § 371 National Stage filing of International Application No. PCT/US2015/10674, filed on Jan. 8, 2015, which claims priority to U.S. Provisional Application No. 61/924,815 filed on Jan. 8, 2014, the content of each application is hereby incorporated by reference in its entirety.

BACKGROUND

Many retail establishments currently require a customer to either fax-in or personally drop off a medical prescription for prescription medication. The customer then typically waits at the retail establishment for the medical prescription to be filled. Once the prescription is filled, the customer then typically pays for the prescription medication by using a traditional cashier who scans the prescription medication and then receives tender from the customer for payment of the prescription medication. This process typically requires the customer to shop for and purchase prescription medication by first providing the medical prescription to the retail establishment, then travelling to the retail establishment and waiting at the retail establishment for the medical prescription to be filled, and finally purchasing the prescription medication at the retail establishment once the medical prescription has been filled.

Having the customer wait at the retail establish once the medical prescription is being filled, and then having the customer pays for the medical prescription medication by using a traditional cashier, takes time since it requires interaction with a cashier, which often detracts from the user's shopping experience. Additionally, as a result of this process, retail establishments have to invest in additional cashiers, and additional time is required from the customer to complete his purchase by having to go to a cashier. It would be desirable to provide a customer and a retail establishment with a method for dispensing and purchasing prescription medication from a retail establishment in a streamlined and timely manner.

SUMMARY

In one aspect, a system for purchasing a pharmaceutical medication is provided. The system includes, but is not limited to, a local device for receiving prescription ready information which notifies a user that the pharmaceutical medication is ready for pick-up and a remote server. The prescription ready information contains general payment options directed to the user. The remote server is connected with the local device. The remote server includes a notification and payment system. Upon receiving the prescription ready information at the local device, the local device transmits purchase instructions to the notification and payment system. The notification and payment system transmits the purchase instructions to a financial computer system in order to obtain a preauthorization for funds, if a general payment option is selected, in order to purchase the pharmaceutical medication.

The scope of the present invention is defined solely by the appended claims and is not affected by the statements within this summary.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

In the description that follows, the subject matter of the application will be described with reference to acts and symbolic representations of operations that are performed by one or more computers, unless indicated otherwise. As such, it will be understood that such acts and operations, which are at times referred to as being computer-executed, include the manipulation by the processing unit of the computer of electrical signals representing data in a structured form. This manipulation transforms the data or maintains it at locations in the memory system of the computer which reconfigures or otherwise alters the operation of the computer in a manner well understood by those skilled in the art. The data structures where data is maintained are physical locations of the memory that have particular properties defined by the format of the data. However, although the subject matter of the application is being described in the foregoing context, it is not meant to be limiting as those skilled in the art will appreciate that some of the acts and operations described hereinafter can also be implemented in hardware, software, and/or firmware and/or some combination thereof.

Figure 1A:
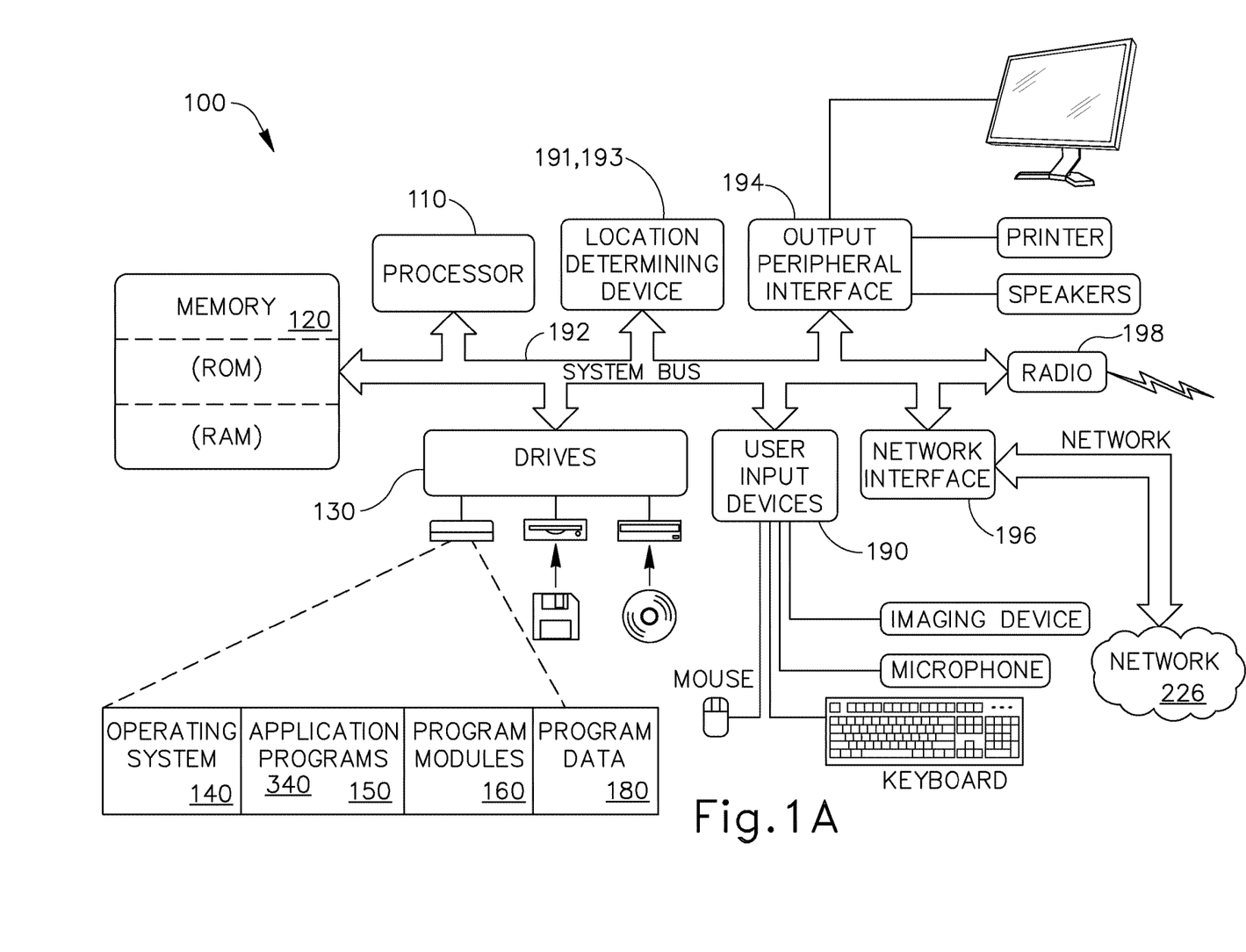
FIG. 1A depicts a block schematic diagram of an exemplary computing system, in accordance with one embodiment of the present invention.

With reference to FIG. 1A, depicted is an exemplary computing system for implementing embodiments. FIG. 1A includes a computer 100, which could be any one of a local device 200 or remote server 240. A local device 200 is any device which is locally accessible by the customer or user, such as a mobile computer, a laptop computer, a mobile phone, an automotive computer system, a touchscreen computer, an automotive navigation system, and a kiosk. A remote server 240 is any computer system which is remote from the user and the local device 200 and receives and transmits information from and to the local device 200. Local device 200 may be a portable device, wherein at least some or all of its components are formed together in a single device which can be carried around by a person.

The computer 100 includes a processor 110, memory 120 and one or more drives 130. The drives 130 and their associated computer readable memory medium provide storage of computer readable instructions, data structures, program modules and other data for the computer 100. Drives 130 can include an operating system 140, application programs 150 such as notification and payment system 340, program modules 160, and program data 180. Computer 100 further includes input devices 190 through which data may enter the computer 100, either automatically or by a user who enters commands and data. Input devices 190 can include an electronic digitizer, a flatbed scanner, a barcode reader, a microphone, a camera, a video camera, a keyboard and a pointing device, commonly referred to as a mouse, a trackball or a touch pad, a pinpad, any USB device, any Bluetooth enabled device, an RFID or NFC device, and a debit card reader. Other input devices may include a joystick, game pad, satellite dish, scanner, and the like. In one or more embodiments, input devices 190 are portable devices that can direct display or instantiation of applications running on processor 110.

In one embodiment, computer 100 includes a location determining device 191 which generates location information that is transmitted to the computer 100. Location determining device 191 is any device which can assist in generating location information or which generates location information, such as a satellite signal receiver which can receive Global Positioning System (GPS) signals or any other radio signals emanating from satellites which can be used to determine location, such as GLONASS signals, Galileo signals, Beidou signals, COMPASS signals, IRNSS signals, and QZSS signals. Additionally, location determining device 191 may include a radio receiver for receiving ground based radio signals, such as GPRS signals or any 2G, 3G, 4G, LTE or other type of commonly transmitted radio signal which may be used along with triangulation software to determine one's location and generate location information. Location determining device 191 may also include a wireless signal receiver and/or transmitter, a computer or a network of computers such as the Internet, a satellite, a compass, a gyroscope, or any combination of such which can generate or be used to generate location information 227. Location information 227 can be useful in that it can provide the retail establishment with an estimated time of arrival, for example, of the user. This estimated time of arrival, can assist the retail establishment in preparing for the arrival of the user, such as by preparing any products 220 purchase by the user for pickup by the user.

Location information 227 includes data which can be used to determine the location of the location determining device 191, the computer 100, or the user of the computer 100. Location information 227 includes details as to the location of the local device 200, such as the coordinates of the local device 200, a name of a street, and/or address, and/or city, and/or state, and/or country in which the local device 200 is in or near. Preferably, location information 227 includes details as to the location of the local device 200 within 100 meters, and preferably within 50 meters, and preferably within 10 meters, and most preferably within 5 meters, and preferably within 3 meters, and preferably within one meter.

Location determining device 191 and other input devices 190 can be connected to processor 110 through a user input interface that is coupled to a system bus 192, but may be connected by other interface and bus structures, such as a parallel port, game port or a universal serial bus (USB). Computers such as computer 100 may also include other peripheral output devices such as speakers, printers, and/or display devices, which may be connected through an output peripheral interface 194 and the like.

In one embodiment, computer 100 includes a radio 198 or other type of communications device for wirelessly transmitting and receiving data for the computer 100 with the aid of an antenna. Radio 198 may wirelessly transmit and receive data or information using a variety of protocols and standards such as WiMAX™, 802.11a/b/g/n, Bluetooth™, 2G, 2.5G, 3G, and 4G, wireless standards. Additionally, in one embodiment, radio 198 may wirelessly transmit and receive data using a Short Message Service (SMS) messaging protocol. The SMS messaging protocol is a text messaging service component of phone, web, or mobile communication systems which uses a standardized communications protocols to allow fixed line or mobile phone devices to exchange short text messages. Many mobile device are capable of transmitting and receiving information using the SMS protocol.

In one embodiment, computer 100 operates in a networked environment using logical connections to one or more remote computers, such as a remote server 240. The remote server 240 may be a personal computer, a server, a router, a network PC, a peer device or other common network node, and may include many if not all of the elements described above relative to computer 100. Networking environments are commonplace in offices, enterprise-wide computer networks, intranets and the Internet. For example, in the subject matter of the present application, computer 100 may comprise the source machine from which data is being migrated, and the remote computer may comprise the destination machine. Note, however, that source and destination machines need not be connected by a network or any other means, but instead, data may be migrated via any media capable of being written by the source platform and read by the destination platform or platforms. When used in a LAN or WLAN networking environment, computer 100 is connected to the LAN through a network interface 196 or an adapter. When used in a WAN networking environment, computer 100 typically includes a modem or other means for establishing communications over the WAN, such as radio 198, to environments such as the Internet. It will be appreciated that other means of establishing a communications link between computer 100 and other computers may be used.

Figure 1B:
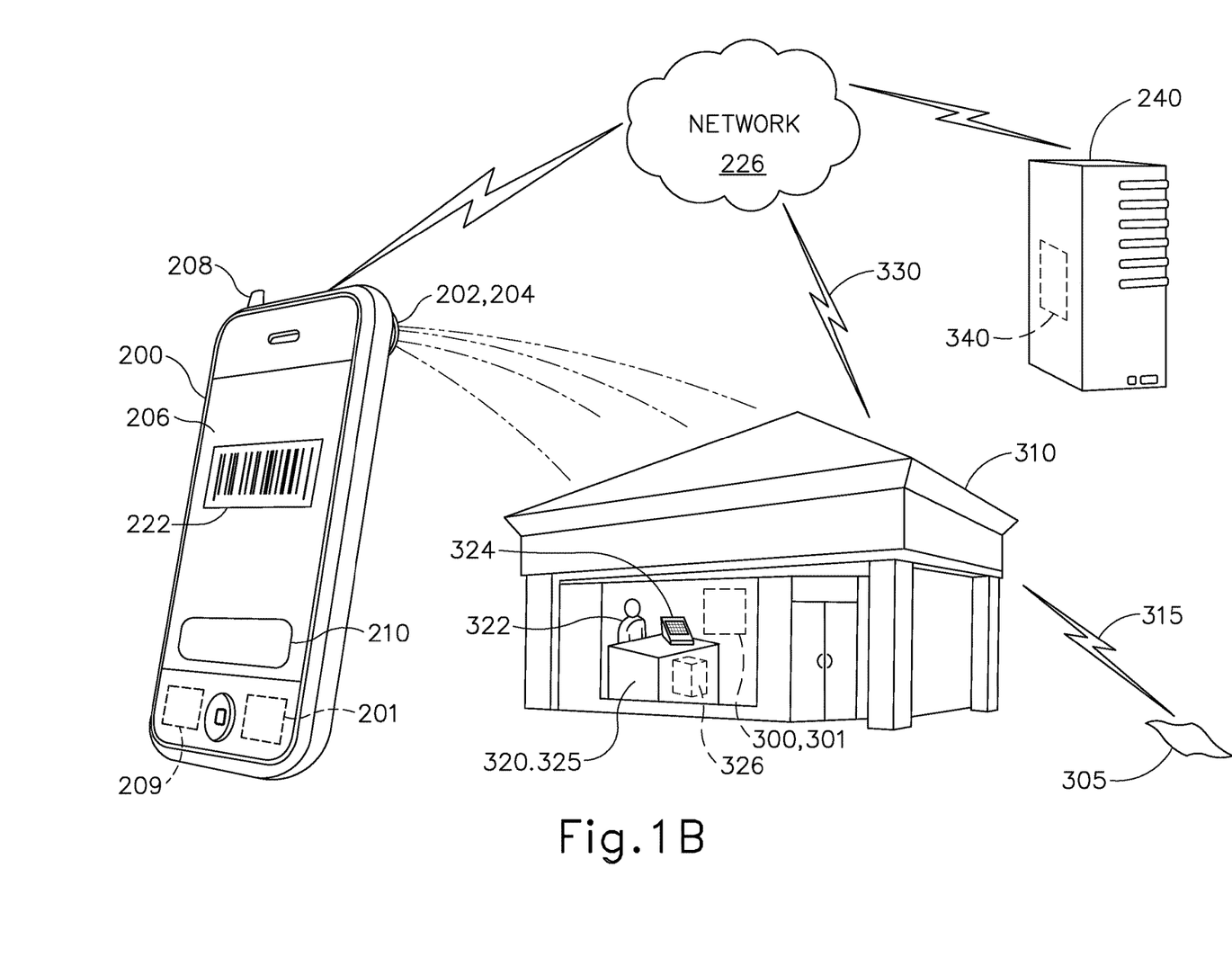
FIG. 1B depicts an illustration of a local or mobile device communicating with a remote server, in accordance with one embodiment of the present invention.

With reference to FIG. 1B, illustrated is an exemplary representation of a local device 200 for receiving notifications and purchasing a product 220 from a retail establishment. As used herein, the term "product" or "product 220" refers to any item or service sold by a retail establishment. "Item" include tangible objects or computer software which may be fixed in a tangible medium that may be purchased from a retail establishment. "Service" includes non-tangible objects or useful labor that does not produce a tangible commodity that may be purchased from a retail establishment. In one embodiment, the product 220 is prescription medication.

In one embodiment, local device 200 includes any transportable, local, mobile, or portable electronic device having a processor 201 for executing applications and a display 206 for displaying information connected with the processor 201, and includes such devices as a personal desktop assistant (PDA), a portable computer, a mobile telephone, a smartphone, a netbook, a mobile vehicular computer, a tablet computer, a kiosk, a handheld scanner, or a point of sale device. Display 206 can use any of a variety of types of display technologies, such as a liquid crystal display (LCD), a cathode-ray tube type display, an electronic ink display, a light emitting diode (LED) type display such as an OLED display, and a plasma display.

In one embodiment, the local device 200 includes a communications device 208. The communications device 208 is connected with the processor 201 and capable of sending and receiving information between one or more other computers connected with the local device 200. Preferably, communications device 208 is capable of wirelessly transmitting signals to another computer, such as remote server 240, using a radio transmitter and a radio receiver connected with an antenna. In one embodiment, the local device 200 includes a scanning module 202 capable of receiving information and converting the information into a format that the processor 201 can read, such as digital data. Preferably, scanning module 202 includes any device which can capture, receive and process information, near-field communication (NFC) sensor, such as a Quick Response (QR) code, a barcode or any image, and includes devices such as a digital scanner, a digital camera, a video camera, a barcode reader, and any other type of digital or analog imaging device.

Preferably, communications device 208 communicates with another computer 100, such as remote server 240, via a network 226 using a network interface 209. Network interface 209 is connected with processor 201 and communications device 208, and preferably disposed within remote device 200.

Network 226 may include any type of network that is capable of sending and receiving communication signals, including signals for multimedia content, images, data and streaming video. Network 226 may include a data network, such as the Internet, an intranet, a local area network (LAN), a wide area network (WAN), a cable network, and other like systems that are capable of transmitting information, such as digital data, and the like. Network 226 may also include a telecommunications network, such as a local telephone network, a long distance telephone network, a cellular telephone network, a satellite communications network, a cable television network and other like communications systems that interact with computer systems to enable transmission of information between local device 200 and another computer such as remote server 240. Network 226 may include more than one network and may include a plurality of different types of networks. Thus, network 226 may include a plurality of data networks, a plurality of telecommunications networks, cable systems, satellite systems and/or a combination of data and telecommunications networks and other like communication systems.

Preferably, network 226 is connected with both local device 200 and remote server 240 and allows for information to be transmitted and shared between local device 200 and remote server 240. Remote server 240 includes any type of computer which can receive, store, process, and transmit information to another computer and includes devices such as a server based computer system capable of interacting with one or more other computer systems. Preferably, the remote server 240 runs notification and payment system 240, or a portion of the notification and payment system 240.

In one embodiment, local device 200 includes location information processing means 193 which allows the local device 200 to determine its location. Location information processing means 193 preferably receives information from a location determining device 191, such a Global Positioning System (GPS) based device, a radio transmitter or receiver, a computer or a network of computers such as the Internet, a satellite, a compass, a gyroscope, manually entered information from the user, or any other device which can be used to detect one's location. Location determining device 191 is in communication with location information processing means 193 and may be remote from or part of the local device 200. Methods or systems for determining one's location, such as using radio triangulation to determine one's location, may be used by the location information processing means 193 to generate location information 227 or location information 227 may be transmitted to the location information processing means 193. Either way, location information processing means 193 enables the local device 200 to determine its location and generates location information 227 as a result.

A retail establishment may be either an online retail establishment which conduct business through the internet or a brick-and-mortar retail establishment which conduct business through a physical store or warehouse. A retail establishment includes a pharmacy, a supermarket, a general retail store, a wholesale store, a charity organization, a restaurant, or any other place which sells goods or services. The term "retail establishment" also includes a retail establishment's agents, such as any third party associated with the retail establishment or working in conjunction with the retail establishment. For example, a third party could be a delivery company working in conjunction with the retail establishment or a company that provides a service to the user or consumer through the retail establishment. Preferably, the retail establishment is a pharmacy or contains a pharmacy which dispenses and sells pharmaceutical medication.

Preferably, local device 200 includes input means 210 for entering information from a user into the local device 200. Input means 210 includes any device which can assist a user to enter information, such as a keyboard, a mouse, a touchpad, a touchscreen, a joystick, a button, a microphone, a camera, and a dial.

Preferably, the product 220 is located within a brick-and-mortar retail establishment or accessible by the brick-and-mortar retail establishment. The product 220 is ordered through the retailer upon receiving a request from the user, the retailer then sends the user the terms of the request such as the price of the product 220 and/or the estimated delivery time. Upon acceptance of the terms of the request by the user, an order for the product is completed. As used herein, an order is any request to purchase a product 220. The order is comprised of information received from a notification and payment system 340 which operates on a computer 100, such as a server 240. The information in the order includes user payment information, and information received from the user, such as purchase instructions, user payment information, and user personal information.

Figure 2:
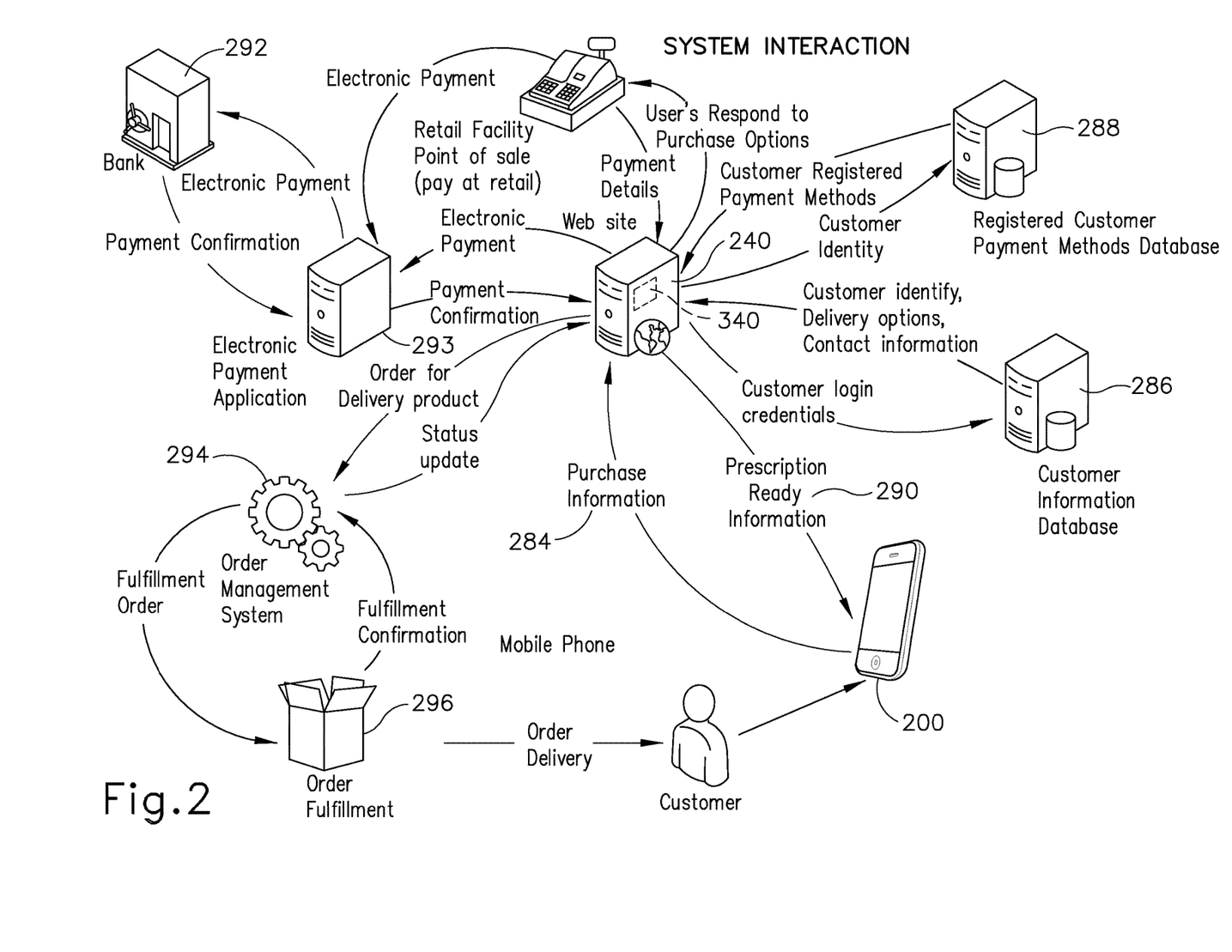
FIG. 2 depicts a system level flowchart of interactions between a customer, a local or mobile device, and a remote server, in accordance with one embodiment of the present invention.

With reference to FIGS. 1B and 2, in one embodiment, the product 220 is a pharmaceutical medication 300, which is to be dispensed from a retail establishment or pharmacy 310. Pharmaceutical medication 300 is a medicinal product, which includes any chemical substance, or product comprising such, intended for use in the medical diagnosis, cure, treatment, or prevention of a disease or ailment. Preferably, the pharmaceutical medication 300 is a prescription medication 301, which requires a medical prescription from a physician in order to obtain the prescription medication 301 from the pharmacy 310 and for the pharmacy 310 to dispense the prescription medication 301 to a user.

Pharmacy 310 dispenses and sells pharmaceutical medication 300 to users and includes a point of sale (POS) system 320, such as a cashier 322, a cash register 324, a self-checkout station, or a drive-thru station 325 which may be connected with or part of the pharmacy 310. Additionally, pharmacy 310 may be a free standing structure or connected with or part of a retail establishment which sells products other than pharmaceutical medications 300.

A retail establishment may be either an online retail establishment which conduct business through the internet or a brick-and-mortar retail establishment which conduct business through a physical store or warehouse. A retail establishment includes a pharmacy, a supermarket, a general retail store, a wholesale store, a charity organization, a restaurant, or any other place which sells goods or services. In one embodiment, the retail establishment is the pharmacy 310 or is an entity which owns the pharmacy 310. Preferably, the product 220 is located within a brick-and-mortar retail establishment or accessible by the brick-and-mortar retail establishment.

When the user requires prescription medication 301, typically, a physician of the user's will issue a medical prescription 305 for the prescription medication 301. The medical prescription 305 includes prescription information 315 which details such things as the user's name or other user identifying information which identifies the user (i.e. a social security number, an address, an insurance account number), the name of the pharmaceutical medication 300 or prescription medication 301, the quantity of pharmaceutical medication 300 or prescription medication 301, the dosage of pharmaceutical medication 300 or prescription medication 301, and the name of the physician of the user's prescribing the medication 300 or 301 or other physician identifying information which identifies the physician of the user's. The prescription information 315 is then transmitted to the pharmacy 310 and employees within the pharmacy 310, and preferably to a remote server 240 in communication with the pharmacy 310 or a computer 326 within the pharmacy 310. The prescription information 315 may be transmitted any one of a number of ways to the pharmacy 310, and to employees within the pharmacy 310, such as by: electronically transmitting an image of the medical prescription 305 to the pharmacy 310 such as via facsimile transmission, delivering the medical prescription 305 or an image of the medical prescription 305 to the pharmacy 310 such as at the drive-thru station 325, electronically transmitting the prescription information 315 directly (such as by using a computer 100) to computer 240 which is in communication with the pharmacy 310 or a computer 326 within the pharmacy 310.

The user may provide the pharmacy 310 with the user's personal information and pre-registered payment information in advance of transmitting the prescription information 315 to the pharmacy 310, in order to expedite the process of filling and paying for the medical prescription 305. For example, the user may provide the user's personal information to an employee of the pharmacy 310 or register with a computer system of the pharmacy 310, such as an online or remote computer of the pharmacy 310, such as remote server 240.

Upon receiving the prescription information 315, the pharmacy 310, preferably through the notification and payment system 340, accesses the user's personal information, which may be stored remotely on the remote server 240 at a customer information database 286, and preferably also accesses the user's pre-registered payment method information which may be stored remotely at a registered customer payment methods database 288. The user's personal information may include the user's identity, name, address, delivery options, contact information, and personal preferences, along with user insurance information which includes details regarding the user's medical insurance plan. The user's payment method information may include any one of the user's pre-registered payment methods associated with the user's account, such as a PayPal™ account or other online payment account information, credit card information, bank account information, and any other information related to a financial payment means which can be used to provide authorization of funds to purchase the product 220. Additionally, the user may enter a new payment method before payment for the product 220 is authorized. The user may enter a payment method either by keying in a new payment method or scanning new payment information from a medium, such as a credit card.

Upon receiving the prescription 305, employees at the pharmacy 310 will begin to fill the medical prescription 305, and the various stages of filling the medical prescription 305 can be communicated the user, and preferably to the user's local device 200, such as by SMS messages. Additionally, once the medical prescription 305 is filled and the pharmaceutical medication 300 is ready for pick-up by the user, the pharmacy 310, and preferably employees of the pharmacy 310, generate prescription ready information 330 preferably using a computer 326 within the pharmacy 310 and then communicates the prescription ready information 330 to the user preferably via the local device 200. The prescription ready information 330 contains information indicating that the user's medical prescription 305 has been filled and that the user's pharmaceutical medication 300 is ready for pick-up by the user. Preferably, the prescription ready information 330 also includes pricing information, such as the amount due for the filled prescription 305. Preferably, the prescription ready information 330 is generated using the user specific information and preferably also uses the prescription information 315.

User specific information is information specific to the user, such as user account information, the user identifying information, user's personal information, user payment information, and user insurance information. Preferably, the prescription ready information 330 contains information which indicates to the user that the medical prescription 305 has been filled and that the pharmaceutical medication 300 is ready for pick-up by the user, or that the pharmaceutical medication 300 will be ready for pick-up by the user at a given time. The prescription ready information 330 may also include location information for the pharmacy 310 at which the pharmaceutical medication 300 will be and even direction to the pharmacy 310. Preferably, the prescription ready information 330 also includes an amount due for the purchase of the medical prescription 305.

In one embodiment, the prescription ready information 330 includes payment options, such as general payment options, while in another embodiment, the payment options are transmitted separately to the local device 200. Payment options may include general payment options and/or specific payment options. General payment options are general payment methods which can be used for a general category of payment, such as "credit card", "online account", "cash", or "checking account." Specific payment options are payment accounts which are specific to the user, such as specific credit card accounts, specific bank or checking accounts, and specific online accounts.

In one embodiment, upon receiving the prescription ready information 330, general payment options are also transmitted to and received by the local device 200. The general payment options are provided to the user for purchasing the pharmaceutical medication 300 ready for pick-up by the user. Preferably, the general payment options provide the user with general payment methods and/or general options to pay or not pay for the pharmaceutical medication 300 in advance of picking up the pharmaceutical medication 300. In one embodiment, the general payment options provide the user with a choice of various general payment methods for a general category of payment, such as "credit card", "online account", "cash", or "checking account."

Preferably, upon selection of a general payment option, the user transmits the selected general payment option to the notification and payment system 340. Preferably, upon receipt of the selected general payment option, the notification and payment system 340 retrieves specific payment options which are specific to the user and related to the selected general payment option, from registered customer payment method database 288 and then transmits the specific payment options to the user at the local device 200. For example, if the notification and payment system 340 receives a selected general payment option of "credit card," the notification and payment system 340 can look up all credit card accounts on file for the user in the registered customer payment methods database 288 and then transmit a list of specific credit card accounts, or specific payment options, to the user at the local device 200.

When the payment options are specific payment options, they are payment options which are unique and specific to the user, such as specific payment accounts or methods from which the user may pay for the pharmaceutical medication 300 (i.e. specific credit card accounts, bank accounts, or online accounts). Preferably, the payment options include a payment identifier for each specific payment option or general payment option from which the user may pay for the pharmaceutical medication 300. For example, the user may be provided with the following payment options: A. Payment via an Online Account, B. Payment via Credit Card A, C. Payment via Credit Card B, D. Payment via Checking Account, or E. No Payment made at this time, whereby the payment identifier would be "A", "B", "C", "D", or "E". The user can then respond to the payment options with purchase instructions which are transmitted from the local device 200 to the remote server 240. The purchase instructions indicate the user's choice of payment option from the provided payment options, and can include a general payment option, a specific payment option, and a payment identifier. Preferably, the purchase instructions are generated by selecting a payment identifier or payment option and transmitting the selected payment identifier or payment option back to the pharmacy 310, such as by sending an SMS message in response to the prescription ready information 330 containing the payment identifier or payment option. Upon receiving the selected payment option, or the selected payment identifier, the user's wishes are carried out either by obtaining authorization or a preauthorization of funds from a financial computer system 292, or nothing needs to be done if the user does not wish to make payment at this time. Preferably the user respond to the payment options using the local device 200, whereby the local device 200 transmits a message to a pharmacy 310 via remote server 240.

In one embodiment, the pharmacy 310 and the user both communicate with each other via the notification and payment system 340, which is preferably residing on the remote server 240. However, the notification and payment system 340 may reside on any one of a number of computers 100, and even multiple computers 100. The remote server 240 may reside internally within the pharmacy 310, and include the computer 326, or on any number of computers 100 which are in communication with each other. Preferably, the notification and payment system 340 generates both the prescription ready information 330 and the payment options. Additionally, in one embodiment, the notification and payment system 340 also receives the user's response to the payment options, such as the payment identifier. Preferably, the notification and payment system 340 is in communication with the financial computer system 292 for obtaining preauthorization or authorization of the user's funds for payment of the pharmaceutical medication 300; the notification and payment system 340 is in communication with a customer information database 286 which contains user identifying information; and the notification and payment system 340 is in communication with a registered customer payment methods database 288 which includes the user's payment accounts or methods from which the user may pay for the pharmaceutical medication 300, as shown in FIG. 2.

In one embodiment, the prescription ready information 330 contains a unique identifier which is used to uniquely identify the user, and preferably used to uniquely identify both the user and the pharmaceutical prescription 305 being filled for the user. In one embodiment, the unique identifier identifies the order for the pharmaceutical prescription 305 being filled for the user. The unique identifier may be the user's name, the user's birth date, an order number, an account number, or any other identifying piece of information which can be used to identify the user, the pharmaceutical prescription 305 being filled for the user, or the order. The unique identifier may include a link to a specific website or application on the local device 200 allowing the user to respond to the pharmacy 310 upon receiving the prescription ready information 330, such as by confirming that the user will pick-up the pharmaceutical medication 300 or pay for the medication 300 using a specific payment method. In one embodiment, all or any information sent between the local device 200 and the remote server 240 is via text messages preferably using an SMS messaging protocol, such as prescription ready information 330, prescription information 315, purchase instructions, general payment options, specific payment options, selected general payment option, selected specific payment option, payment identifiers, unique identifiers, and any other such information.

In one embodiment, a unique mobile identifier may also be communicated to the notification and payment system 340 for the purposes of identifying the user via the local device 200. Preferably, the local device 200 transmits the unique mobile identifier, to the notification and payment system 340. The unique mobile identifier includes any information which can be generated by the local device 200, is specific to the local device 200, and can uniquely identify the user, such as a mobile phone number, a mobile IMEI number, or other such information. The unique mobile identifier may be provided when the local device 200 sends messages back to the notification and payment system 340 or may be provided at some later point in time. In one embodiment, both the unique identifier and the unique mobile identifier are transmitted to the notification and payment system 340 for the purposes of identifying the user, the local device 200, or the order.

Figure 3:
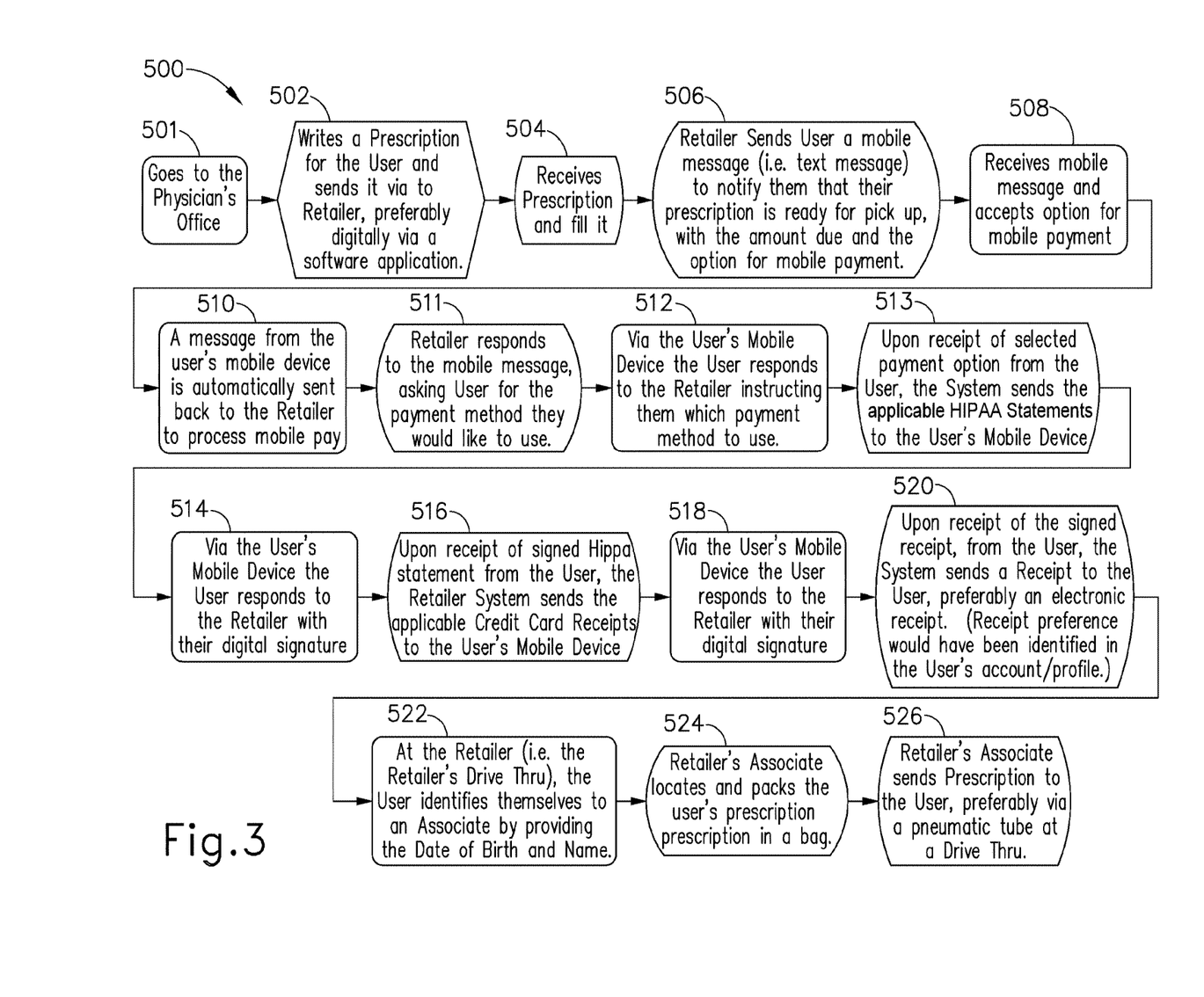
FIG. 3 depicts a system level flowchart of interactions between a customer or user, a local or mobile device, and a remote server, in accordance with one embodiment of the present invention.

With reference to FIGS. 2 and 3, shown is a method 500 for purchasing pharmaceutical medication 300 using a local device 200. In operation, the method begins at block 501 whereby the user goes to the user's physician's office in order to treat an ailment. Then at block 502, the user's physician writes a medical prescription 305 for the user in order to help cure the user's ailment, and then transmits the medical prescription 305, and specifically the prescription information 315 within the medical prescription 305, to the user's pharmacy 310 and employees within the pharmacy 310, preferably via a facsimile transmission or via an electronic transmission to remote server 240 in communication with the pharmacy 310 or a computer 326 within the pharmacy 310.

Then at block 504, the retail establishment, and specifically the pharmacy 310, receives the medical prescription 305 and then begins to fills the medical prescription 305.

Additionally, the various stages of filling the medical prescription 305 can be communicated the user, and preferably to the user's local device 200, such as by SMS messages.

At block 506, once the medical prescription 305 is filled and the pharmaceutical medication 300 is ready for pick-up by the user, the pharmacy 310, and preferably employees of the pharmacy 310, generate prescription ready information 330, preferably using a computer 326 within the pharmacy 310, communicate the prescription ready information 330 to the user preferably via the local device 200. In one embodiment, the pharmacy 310 send the user an SMS message containing the prescription ready information 330 to notify the user that the medical prescription 305 is ready for pick-up. Preferably, the prescription ready information 330 includes an amount due along with general payment options allowing the user to pay for the pharmaceutical medication 300 using the local device 200, and preferably by using SMS messages via the local device.

Moving to blocks 508, the user then receives the prescription ready information 330, which preferably includes an amount due along with payment options, and accepts a payment option for payment via the local device 200. At block 510, the user transmits a message, to the pharmacy 310, preferably via server 240, in response to the prescription ready information 330. Preferably, the message includes purchase instructions which include a selected payment option (i.e. a selected general payment option or a selected specific payment option), or payment identifier, indicating which payment option, if any, the user wishes to execute at this moment.

In one embodiment, the payment option, or payment identifier, selected is a general payment option for a general category of payment, such as "credit card" or "checking account." In this embodiment, the method then moves to block 511, whereby the pharmacy 310 transmits via the notification and payment system 340, a message including specific payment options within the selected general category of payment, such as "Credit Card A" or "Checking Account B" whereby the user is asked to select a specific payment option. In some embodiments, the user may have preselected or "default" specific payment options, and it may not be necessary to ask the user to select a specific payment option and then transmit a selected specific payment option to the notification and payment system 340.

Moving to block 512, the user then respond to the pharmacy 310's request for detailed and specific payment options within the selected general category of payment options, preferably using the local device 200, and preferably by sending an SMS message containing detailed purchase instructions via the local device 200.

At block 513, in one embodiment, upon receiving the selected payment option from the user, the pharmacy 310 via the notification and payment system 340, sends applicable 14 HIPAA statements to the user's local device 200, whereby the user is preferably instructed to read the HIPAA statements, and the user responds with a digital signature acknowledging that the user has read the HIPAA statements at block 514.

Moving to block 516, upon receipt of the digital signature acknowledging that the user has read the HIPAA Statements, the pharmacy 310 transmits via the notification and payment system 340 applicable purchase receipts, such as a credit card receipt if a credit card payment option is chosen, to the local device 200 for signature by the user.

At block 518, via the user's local device 200, the user may respond to the applicable purchase receipts by transmitting a digital signature to the pharmacy 310 via the notification and payment system 340. Then at block 520, upon receiving the digital signature indicating the user's acknowledgement and acceptance of conditions listed on the applicable purchase receipts, the notification and payment system 340 sends a receipt to the user, preferably an electronic receipt. The receipt may be sent electronically via e-mail, or via SMS message to the user's local device 200. Preferably, the user will indicate his preference in advance in a user account profile of the user.

Additionally, the pharmacy 310 will then communicate with a financial computer system 292 and receive authorization for funds in response to receiving the user's acknowledgement and acceptance of conditions listed on the applicable purchase receipts. Upon providing the purchase instructions to the notification and payment system 340, the notification and payment system 340 communicates with a payment processing application that is connected to a financial computer system 292 of a financial institution in order to obtain a preauthorization for funds to be used in payment for the order of products 220.

Upon receiving a preauthorization of funds from the financial computer system 292, the notification and payment system 340 communicates with and transmits to the pharmacy 310, or with computers 326 within the pharmacy 310, to provides them with an authorization of payment code used to indicate that funds have been authorized for payment of the product 220 and allow the product 220 to be given to the user.

Preferably, before payment is made or authorized, the amount of the order is calculated and determined based on, but not limited to item prices, taxes, sale promotions, discounts, rebates, coupons, fees (delivery, installation, and warranty), local charges, deposit fees. Upon calculating the amount of the order, an order sale recording application or system documents a sale of the order, such as the transfer of ownership and removal of an item from the retail establishment's inventory. For each order, single payment amount is calculated.

In one embodiment, payment is completed for the order via a payment processing application that is connected to the financial computer system 292, wherein the notification and payment system 340 provides payment information to the payment processing application which in turn sends payment information to the financial computer system 292 and receives authorization information from the financial computer system 292.

Moving to block 522, the user will proceed to arrive at the pharmacy 310, preferably at the drive-thru station 325, and identify himself or herself to an employee of the pharmacy 310 by providing user identifying information, such as the user's date of birth and/or name. Then at block 524, the pharmacy 310 will locate and provide the user with the filled prescription, or pharmaceutical medication 300, preferably packaged in packaging such as a container and/or a bag. Then at block 526, in one embodiment, the pharmacy 310 delivers the pharmaceutical medication 300 to the user, preferably via a pneumatic tube at the drive-thru station 325.

As a result, by simply sending messages back and forth between the notification and payment system 340 and the user's local device, such as SMS messages, the user is able to be notified that the user's prescription 305 has been filled, then the user is provided with payment options for paying for the filled prescription 305, and the user is able to pay for the filled prescription 305 before arriving at the pharmacy 310, streamlining the method for dispensing and purchasing prescription medication from a retail establishment for the user.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a computer readable memory medium such as a magnetic medium like a floppy disk, a hard disk drive, and magnetic tape; an optical medium like a Compact Disc (CD), a Digital Video Disk (DVD), and a Blu-ray Disc; computer memory like random access memory (RAM), flash memory, and read only memory (ROM); and a transmission type medium such as a digital and/or an analog communication medium like a fiber optic cable, a waveguide, a wired communications link, and a wireless communication link.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into comprehensive devices and/or processes and/or systems via a reasonable amount of experimentation. Those having skill in the art will recognize that examples of such comprehensive devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Quest, Southwestern Bell, etc.); or (g) a wired/wireless services entity such as Sprint, Cingular, Nextel, etc.), etc.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. Accordingly, the invention is not to be restricted except in light of the appended claims and their equivalents.

The invention claimed is:

1. A system comprising:
a user database that stores user information;
a remote server, communicatively in communication with a first computing system, a second computing system, a third-party system and the user database, the remote server configured to:
receive prescription information for a user from a medical practitioner;
store the prescription information for the user in the user database;
query the user database using input received from the user to retrieve a unique identifier associated with both the user and the prescription information for the user, the unique identifier is one of: a name of the user, a birthdate of the user, an order number, or an account number;
include a link in the unique identifier subsequent to retrieving the unique identifier from the user database;
transmit a message including the unique identifier to a local device associated with the user, the local device is configured to transmit location information of the local device;
receive instructions from the local device based on selection of the link included in the unique identifier by the local device, the received instructions including at least a digital signature and a unique mobile identifier;
determine whether the user is authorized to receive sensitive information in compliance with HIPAA regulations and has consented to the HIPAA terms based at least in part on the digital signature; and
determine whether the local device is authorized to receive sensitive information based at least in part on the unique mobile identifier;
in response to the determination that the user is authorized to receive information and the local device is authorized to receive sensitive information, retrieve a profile associated with the user from the first computing system based on the unique identifier to identify the user;
retrieve sensitive information associated with the user from the second computing system based on the profile;
transmit the sensitive information associated with the user and a pre-authorization request to the third-party system;
obtain preauthorization from the third party system in response to the instructions;
track geographic coordinates of the local device based on the location information received from the local device;
estimate an arrival time of the user based on the geographic coordinates of the local device;
in response to preauthorization and the estimated arrival time, initiate at least one operation in preparation for arrival of the user;
send, from the remote server, a prescription ready message to the local device including an amount due for the prescription and an option for mobile payment; and
receive, at the remote server, a selection of mobile payment method in response to the prescription ready message and process the payment for the prescription prior to the arrival of the user at a pharmacy.

2. The system in claim 1, wherein the remote server uses a Short Message Service messaging protocol to transmit the message.

3. The system in claim 1, wherein the message can include destination location.

4. A method comprising:
receiving prescription information for a user from a medical practitioner from a remote server communicatively coupled to a first computing system, a second computing system, a third-party system and a user database storing user information;
storing, via the remote server, the prescription information for the user in the user database;
querying, via the remote server communicatively coupled to a first computing system, a second computing system, a third-party system and a user database storing user information, the user database using input received from a user to retrieve a unique identifier associated with both the user and the prescription information for the user, the unique identifier is one of: a name of the user, a birthdate of the user, an order number, or an account number;
including, via the remote server, a link in the unique identifier subsequent to retrieving the unique identifier from the user database;
transmitting, via the remote server, a message including the unique identifier to a local device associated with the user, the local device is configured to transmit location information of the local device;
receiving, via the remote server, instructions from the local device based on selection of the link included in the unique identifier by the local device, the received instructions including at least a digital signature and a unique mobile identifier;
receiving, via the remote server, a digital signature from the local device;
determining, whether the user is authorized to receive sensitive information based at least in part on the digital signature in compliance with HIPAA regulations and has consented to the HIPAA terms; and
determining whether the local device is authorized to receive sensitive information based at least in part on the unique mobile identifier;
in response to the determination that the user is authorized to receive information and the local device is authorized to receive sensitive information, retrieving, via the remote server, a profile associated with the user from the first computing system based on the unique identifier to identify the user;
retrieving, via the remote server, sensitive information associated with the user from the second computing system based on the profile;
transmitting, via the remote server, the sensitive information associated with the user and a pre-authorization request to the third-party system;
obtaining, via the remote server, preauthorization from the third-party system in response to the instructions;
tracking, via the remote server, geographic coordinates of the local device;
estimating, via the remote server, an arrival time of the user based on the geographic coordinates of the local device based on the location information received from the local device;
in response to preauthorization and the estimated arrival time, initiating, via the remote server, at least one operation in preparation for arrival of the user;

sending, from the remote server, a prescription ready message to the local device including an amount due for the prescription and an option for mobile payment; and receiving, at the remote server, a selection of mobile payment method in response to the prescription ready message and processing the payment for the prescription prior to the arrival of the user at a pharmacy.

5. The method in claim 4, wherein the remote server uses a Short Message Service messaging protocol to transmit the message.

6. The method in claim 4, wherein the message can include a destination location.

7. A method comprising:
transmitting a request from a local device to a remote server, the local device including a location module and an application, the request including user information associated with a user of the local device;

receiving, via the local device, a message including a unique identifier associated with both the user and the prescription information for the user in response to the request, the unique identifier including a link configured to automatically launch the application on the local device, the unique identifier is one of: a name of the user, a birthdate of the user, an order number, or an account number;

transmitting, via the application on the local device, instructions to a remote server for preauthorization;

transmitting, via the application on the local device, instructions to a remote server including a digital signature and a unique mobile identifier; and transmitting, via the location module of the local device, geographic coordinates of the local device to the remote server, the remote server is in communication with a first computing system, a second computing system, and a user database and the remote server is configured to determine whether the user is authorized to receive sensitive information based at least in part on the digital signature in compliance with HIPAA regulations and has consented to the HIPAA terms;

determine whether the local device is authorize to receive sensitive information based at least in part on the unique mobile identifier, retrieve a profile associated with the user from the first computing system based on the unique identifier to identify the user, retrieve sensitive information associated with the user from the second computing system based on the profile, and transmit the sensitive information associated with the user and a pre-authorization request to a third-party system, the preauthorization and the geographic coordinates of the local device initiate at least one operation via the remote server;

receiving, at the local device and from the remote server, a prescription ready message including an amount due for the prescription and an option for mobile payment; and receiving, in response to the prescription ready message, and sending a selection of mobile payment method to the remote server for processing the payment for the prescription prior to the arrival of the user at a pharmacy.

8. The method in claim 7, wherein the local device receives the message using a Short Message Service messaging.

9. The method in claim 7, wherein the message includes a destination location.

10. The method in claim 9, calculating, via the location module of the local device the distance between the local device and the destination location.

11. The method in claim 10, transmitting, via the location module of the local device, geographic coordinates to the remote server upon satisfying specified distance intervals.

12. The system of claim 1, wherein the remote server uses a Short Message Service messaging protocol to transmit the messages back and forth between the local device and the remote server to pay for the filled prescription before arriving at the pharmacy; and the remote server receives input from an employee of the pharmacy to verify the identity of the user at the pharmacy before locating and delivering the filled prescription.

13. The method in claim 4, wherein the remote servers use a Short Message Service messaging protocol to transmit messages back and forth between the local device and the remote server to pay for the filled prescription before arriving at the pharmacy; and the remote server receives input from an employee of the pharmacy to verify the identity of the user at the pharmacy before locating and delivering the filled prescription.

14. The method in claim 7, wherein the remote servers use a Short Message Service messaging protocol to transmit messages back and forth between the local device and the remote server to pay for the filled prescription before arriving at the pharmacy; and the remote server receives input from an employee of the pharmacy to verify the identity of the user at the pharmacy before locating and delivering the filled prescription.

* * * * *